United States Patent [19]

Hentschel et al.

[11] 4,269,979

[45] May 26, 1981

[54] PROCESS FOR THE PRODUCTION OF SUSPENSION OR SOLUTION OF CYANURIC CHLORIDE IN ORGANIC SOLVENTS (II)

[75] Inventors: Klaus Hentschel, Kalmthout, Belgium; Friedrich Bittner, Bad Soden; Gerd Schreyer, Hanau, both of Fed. Rep. of Germany

[73] Assignee: Deutsche Gold- und Silber-Scheideanstalt vormals Roessler, Frankfurt, Fed. Rep. of Germany

[21] Appl. No.: 94,874

[22] Filed: Nov. 16, 1979

[30] Foreign Application Priority Data

Nov. 20, 1978 [DE] Fed. Rep. of Germany ....... 2850243

[51] Int. Cl.³ .......................................... C07D 251/28
[52] U.S. Cl. .................................................... 544/190
[58] Field of Search ......................................... 544/190

[56] References Cited

U.S. PATENT DOCUMENTS

| | | | |
|---|---|---|---|
| 3,256,070 | 6/1966 | Trickey | 23/294 |
| 3,925,377 | 12/1975 | Geiger | 260/248 |

FOREIGN PATENT DOCUMENTS 1545840 10/1969 Fed. Rep. of Germany .
1670731 12/1970 Fed. Rep. of Germany .
2332636 1/1975 Fed. Rep. of Germany .

OTHER PUBLICATIONS

Ullmann, "Enzyklopadie der technischen Chemie", 3rd Ed. (1954), vol. 1, pp. 743–744 and 769–770, vol. 5, pp. 624–625.

Primary Examiner—John M. Ford
Attorney, Agent, or Firm—Cushman, Darby & Cushman

[57] ABSTRACT

Finely divided suspensions of cyanuric chloride in organic solvents which are practically water free are prepared at high mixing velocities and low temperatures by introducing liquid cyanuric chloride through a nozzle in the upper portion of the mixing apparatus in countercurrent flow to upwardly flowing solvent introduced from at least one lower nozzle above a breast shaped constriction in the lower open portion of the apparatus. In this way the chamber walls are always covered with an unbroken layer of liquid. The process can be carried out at normal, reduced or elevated pressure. At reduced pressure by evaporation of the solvent there is simultaneously a cooling of the system.

7 Claims, 3 Drawing Figures

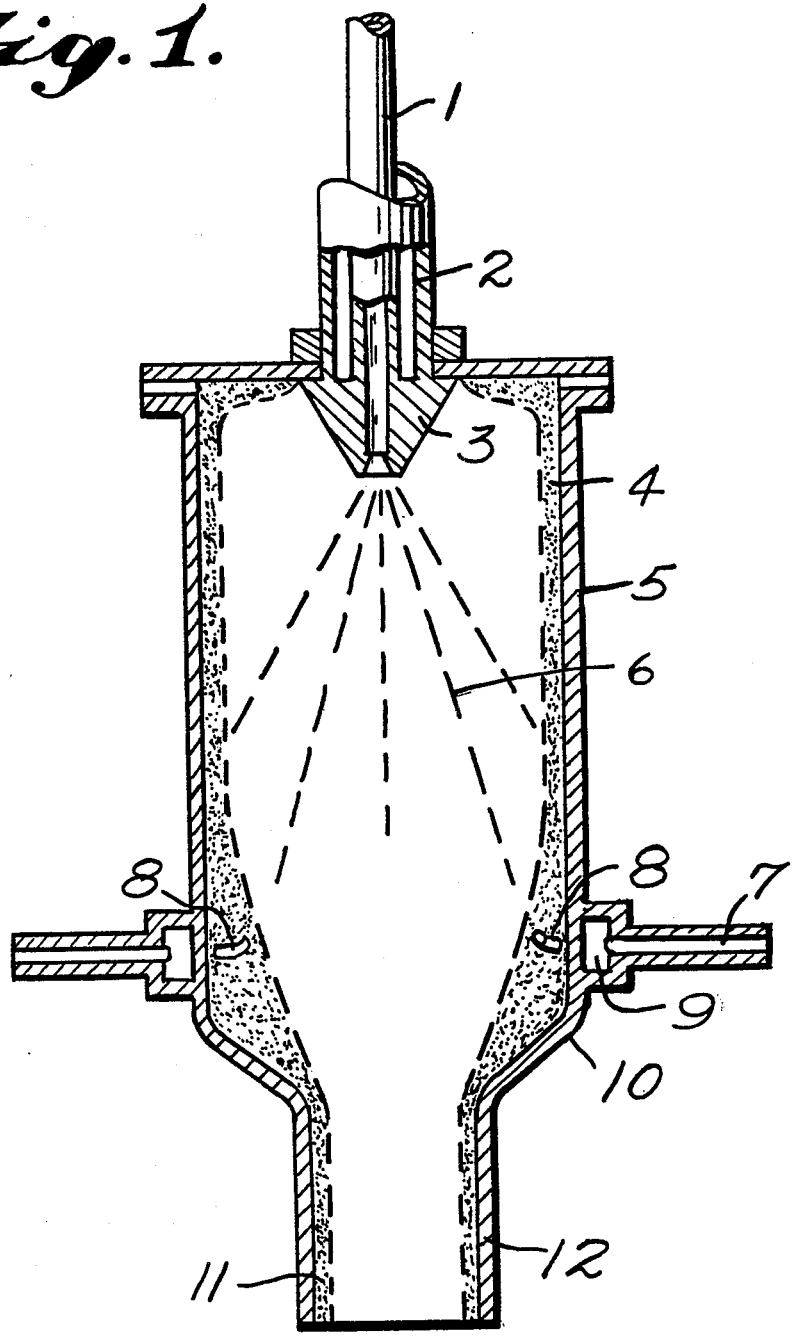

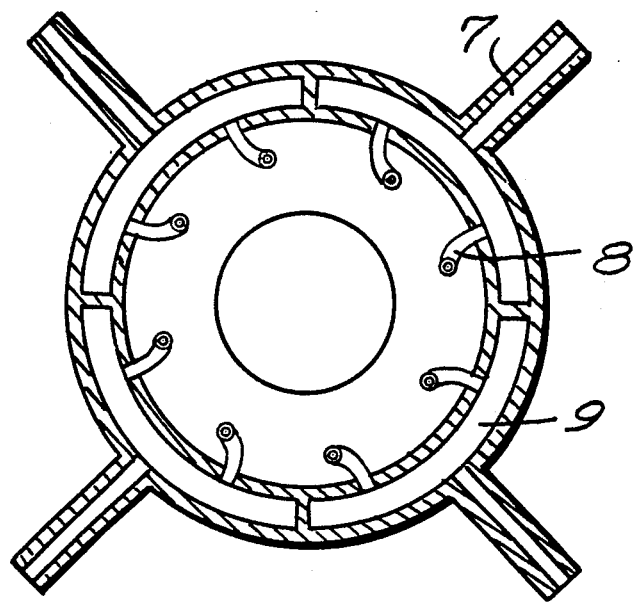
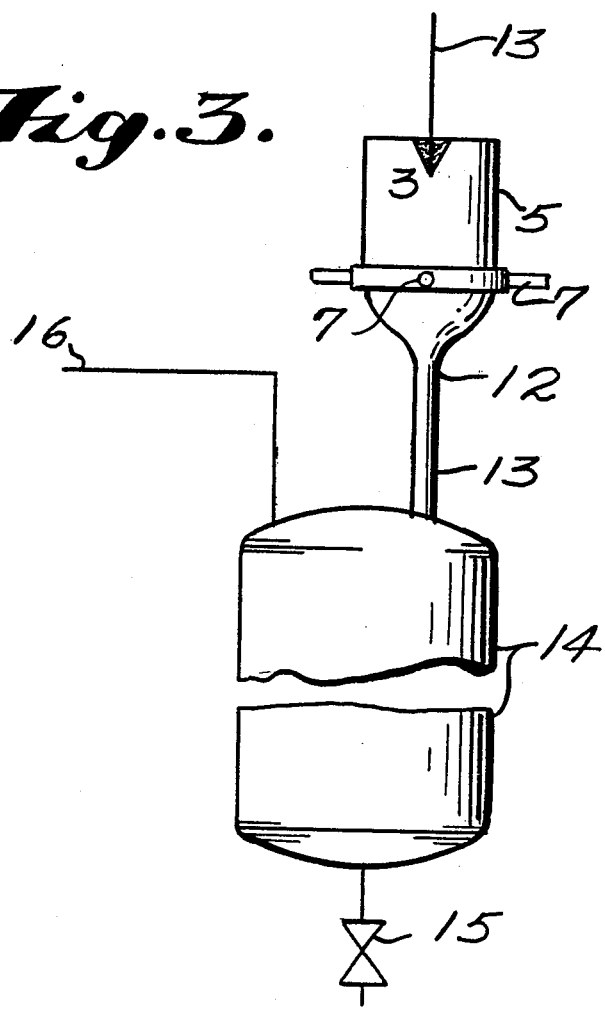

PROCESS FOR THE PRODUCTION OF SUSPENSION OR SOLUTION OF CYANURIC CHLORIDE IN ORGANIC SOLVENTS (II)

BACKGROUND OF THE INVENTION

Cyanuric chloride which is produced by the trimerization of cyanogen chloride with the help of catalysts, above all activated carbon, as is known is a very interesting intermediate product in various industrial sectors such as the production of dyestuffs and products for the textile industry, as well as for pharmaceuticals, products for agriculture, as well as for the synthetic resin, rubber and explosive industries.

As is known after the trimerization cyanuric chloride is obtained in gaseous form, together with unreacted cyanogen chloride and chlorine, as well as byproducts.

For a long time it was customary to convert this gaseous reaction mixture directly into solid cyanuric chloride, e.g. by leading the gaseous mixture into a chamber cooled from outside (see Ullmann, Enzyklopädie der technische n Chemie, 3rd edition, 1954 Vol. 5, pages 624–625 and 4th edition, 1975 Vol. 9, pages 652), or by introducing it into a ball mill cooled with water according to the process of Trickey U.S. Pat. No. 3,256,070.

Solid cyanuric chloride generally is obtained in powder form and until now has been further processed predominantly in this form.

In order to increase its reaction velocity in the further processing it is desirable to have the cyanuric chloride present either in finely divided or dissolved form.

For this purpose there are known a series of processes in which cyanuric chloride in solid form is introduced into an organic solvent (Tandon, German AS No. 1964619) in with (German OS No. 1545840) or into strongly cooled organic solvent-water systems (Granuer, German AS No. 1695177) whereupon the thus obtained cyanuric chloride solutions or suspensions are reacted as soon as possible after their production.

In the production of suspensions of solid cyanuric chloride in pure organic solvents, however, there are obtained relatively coarse grained suspensions whose further processing leads to difficulties. Solutions of cyanuric chloride in the organic solvents generally always are present in lower concentrations; at higher concentrations on the contrary there are formed suspensions of cyanuric chloride.

An object of the invention is the development of a process for the production of fine grained suspensions or solutions of cyanuric chloride in pure organic solvents.

BRIEF DESCRIPTION OF THE DRAWINGS

FIG. 1 is a vertical sectional elevation of one form of apparatus suitable for carrying out the process of the invention;

FIG. 2 is a cross sectional view along the line 2—2 of FIG. 1; and

FIG. 3 is a schematic view of apparatus for carrying out the invention.

SUMMARY OF THE INVENTION

It has now been found that suspensions or solutions of cyanuric chloride can be produced while avoiding or very greatly reducing the hydrolysis of cyanuric chloride by bringing into contact liquid cyanuric chloride and organic solvent with the help of a nozzle if liquid cyanuric chloride which is preferably free from chlorine and cyanogen chloride is sprayed into a container at temperatures in its molten range, if necessary in the presence of an inert gas, through a nozzle, preferably a spray nozzle, which is located in the head of a tubular container, during which this tubular container is closed or closeable at the top and downwardly therefrom is constricted breast shaped to a discharge opening and with which the organic solvent discharges through one or preferably several nozzles, preferably polished steel nozzles, which are located above the constriction and consist of one or more tangential spray agencies arranged in one or more rows which are arranged slightly above in the direction of the upper closing device or are arranged in the direction of the nozzle located in the upper portion and form a liquid layer along the entire chamber walls up to the nozzle for the cyanuric chloride, whereby the thickness of this layer at the breast shaped restriction is greater than at the rest of the chamber walls, and in which the sprayed cyanuric chloride enters.

The liquid cyanuric chloride is preferably introduced into the nozzle through a heated conduit.

By using the described apparatus it is possible to so distribute the organic solvent at the chamber walls that the liquid layer at the breast shaped constriction is thicker than at the remaining chamber walls.

By the expression used in the glass art: "breast shaped constriction" is meant a constriction which does not proceed steeply, but in a flat S curve going from the wall of the tubular container to the discharge opening. Corresponding constrictions are also present in red wine bottles at the transition from the true bottle to the neck.

The constriction in the tubular container can preferably always begin where about 50% of the sprayed particles meet the liquid layer built up on the wall. Preferably this is the case in the lower third of the tubular container.

The size of the diameter of the discharge opening of itself is not critical. Naturally it depends on the viscosity of the medium being discharged and must have at least such a size that air can enter.

The discharge opening is preferably converted into a discharge tube which has any desired diameter, preferably however, the same diameter or larger than the discharge opening.

The nozzle or nozzles for the organic solvent to be sure can be arranged at any place in the tubular container above the constriction, but preferably are located in the region directly above the breast shaped constriction.

As the tangentially arranged spray agencies, there can be used small tubes or nozzles as well as openings in the chamber walls or, with the presence of a feed ring, in its chamber walls.

Preferably there are used small tubes.

The tubular container described has the great advantage that it can be operated not only at an atmospheric pressure but also at reduced pressure. Thus without doing anything further it permits the adjustment proceeding from atmospheric pressure to reduced pressure of 0.01 bar.

At reduced pressure a portion of the solvent evaporates through which a cooling of the solution of suspensions forming takes place. The mixing temperature in this way lets itself be held readily to a low level which is very essential for a continuous procedure.

Previously it was not possible to regulate the mixing temperature in this manner.

As organic solvents there are employed solvents having a water content of less than 0.1 weight % water.

These types of solvents are for example, the straight or branched chain alkanes having 3 to 17 carbon atoms, e.g. propane, butane, pentane, hexane, heptane, octane, decane, dodecane, hexadecane, heptadecane, 2-methylheptane, 2,2,4-trimethylpentane, cycloalkanes such as cyclopentane, cyclohexane as well as decalin, aromatic hydrocarbons such as benzene, toluene, xylene, ethyl benzene, halogenated hydrocarbons such as methylene chloride, chloroform, carbon tetrachloride, monochloroethylene, dichloroethylene, trichloroethylene, tetrachloroethylene, trichloroethane, chlorofluoroalkanes such as trichlorotrifluoroethane, halogenated aromatic hydrocarbons such as chlorobenzenes, e.g., chlorobenzene, and o-dichlorobenzene, chlorofluorobenzenes, o-chlorofluorobenzene, p-chlorofluorobenzene and m-chlorobenzotrifluoride, as well as ketones such as acetone, methyl ethyl ketone, diethyl ketone, methyl isobutyl ketone or cyclohexanone, or esters such as alkyl alkanoates, e.g. ethyl acetate, methyl acetate, butyl acetate, methyl butyrate, methyl propionate or ethers such as diethyl ether, diisopropyl ether, dibutyl ether, methyl butyl ether, dioxane or alcohols, e.g., alkanols such as isopropyl alcohol, methyl alcohol, ethyl alcohol, n-propyl alcohol, and butyl alcohol.

Especially preferred solvents are dioxane, benzene, toluene or methylene chloride. It is also possible to employ a chloride in mixtures of the solvents mentioned above.

The solvents mentioned are added at room temperature or lower temperature up to shortly before the solidification point.

The mixing temperature arising according to the process of the invention generally are in the range of 10 to 15° C. although this can be varied.

The mixing temperature naturally depends on both the mixing ratio "solvent-cyanuric chloride melt" which generally are in the range of 6:1 to 1:1, as well as the, if necessary, applied reduced pressure.

A suitable apparatus for the recovery of the mentioned cyanuric chloride suspensions or solutions is described and claimed in Hentschel application Ser. No. 94,803 filed Nov. 15, 1979 and entitled "Apparatus for Bringing Liquids in Contact" which is operated in the following manner.

As shown in FIG. 1 the liquid cyanuric chloride in supply line 1 is led through a coaxial heater 2 via a unary or binary nozzle 3 into the mixing chamber 5, i.e., the tubular container 5.

The solvent being brought into contact with the sprayed material goes through separate supply lines 7 into a distribution ring having separate chamber segments 9, see also FIG. 2. The solvent is injected tangentially from these chamber segments via the slightly upwardly directed spray systems into the mixing chamber 5.

When using only one supply and only one spray organ, e.g. opening into the mixing chamber 5, the supply 7 passes directly into the spray opening 8 and the segmented chamber 9 is eliminated.

Besides the component in the circumferential direction the solvent jet has a velocity component in the axial direction. Therethrough the liquid reaches the wall of the mixing chamber 5. There it builds a liquid layer 4.

If different solvents are supplied through the supply lines 7, 8 and 9 into the mixing chamber 5, there occurs here an intensive thorough mixing of the supplied liquids, whose intensity can be increased still more by introducing a gas or vapors of the solvent via the spray system 8.

The cyanuric chloride leaving the nozzle 3 is sprayed into the liquid layer 4. The spray angle for the cyanuric chloride sprayed out of nozzle 3 can be between 15 and 150° preferably between 15 and 120°.

The shape of the spray varies from hollow or solid cone up to an unarranged mist, according to the type of nozzle.

Upon entering the spray particles 6 solidify and/or the sprayed cyanuric chloride dissolves in the liquid layer. The energy brought in is given up to the liquid layer, independent of the pressure in the tubular container.

The discharging mixture which leaves the tubular container 5 through the discharge opening 12 goes into container 14 which can be directly or via line 13 connected, if necessary detachably, to the discharge opening 12 of the container 5.

In this way, it is possible to establish any desired pressure, i.e. any desired reduced pressure or superatmospheric pressure in tubular container 5 and container 14 through known apparatus which are connected via line 16 with the container 14, see FIG. 3. (The known apparatus for regulating the pressure, however, are not shown in FIG. 3.)

The mixture is withdrawn at the discharge 15. The container 14, however, in a given case can also serve as a reaction container for a further treatment or reaction.

However, it is also possible to apply reduced or superatmospheric pressure directly into the discharge line 13 through the known apparatus and to convey away the discharge mixture out of line 13 and omit an intermediate connection of container 14.

The apparatuses 5 and 14 shown in FIGS. 1 and 3, in a given case line 13 also can be heated or cooled in known manner, according to requirements, see, e.g. Ullmann, Enzyklopadie der technischen Chemie, Vol. 1, 3rd edition, 1951, pages 743-744 and 769-770.

Likewise as materials of constructions there can be used known materials, loc. cit.

The volume of tubular container 5 is determined by the properties of the liquids used, whereby the path of the sprayed particles 6 to the impingement on the liquid layer 4 should be held as short as possible.

Through this it is possible to carry out relatively large throughputs in a very small tubular container, e.g., the volume in Example 1 is about 1.2 liters.

By establishing a specific pressure, such as a reduced pressure, in the tubular shaped container 5 the heat energy of the sprayed cyanuric chloride in contact with the liquid layer can be carried away.

The suspension or solution of cyanuric chloride produced in the particular solvent leaves the mixing chamber through the discharge outlet 12.

To improve the formation of the solvent layer the spray systems 8 tangential to the mixing chamber are directly slightly upwardly. The exact angle of bending is so adjusted according to the solvent that the liquid layer reaches up to the nozzle, but does not touch it.

Through the breast shaped constriction and the thicker liquid layer produced at this wall position thereby there results, despite the outlet opening, that the remaining chamber walls always are covered with a uniform, i.e. uninterrupted layer of solvent. Through this there is guaranteed a high mixing velocity.

The spray cone of the liquid cyanuric chloride is designated by the number 6.

The number of inlet lines 7 depends on the particular case.

Thus in feeding in only a single material one supply line is sufficient, however, for better distribution of this material there has also proven as desirable to use several supply lines, see for example FIG. 2; even using several components which also can be simultaneously introduced as a mixture the distribution ring described for example in FIG. 2 is suitable.

Liquid cyanuric chloride can be obtained according to known process, e.g. according to Geiger, German Pat. No. 2,322,636 and related Geiger U.S. Pat. No. 3,925,377. The entire disclosure of the Geiger U.S. patent is hereby incorporated by reference and relied upon.

Preferably according to the process of the invention there is employed a liquid cyanuric chloride whose temperature is 170° C. and which is free from chlorine and cyanogen chloride. For freeing from chlorine and cyanogen chloride known processes are suitable, as e.g. dephlegmatization.

The technological advance of the process of the invention is that the cyanuric chloride suspension obtained is very fine grained and there is avoided the formation of any clumps, as can occur even through the simple running in of liquid cyanuric chloride into organic solvents. Through this the danger of an increased reaction time of the cyanuric chloride with subsequent reactions is no longer possible, which formerly could readily lead to side reactions.

However, it is also material that for the first time there can be produced solutions or suspensions of cyanuric chloride continuously according to the requirements of the moment.

Even solvents which of themselves are water-free but by reaction with cyanuric chloride or through self condensation split off water, e.g. ketones, alcohols or esters, can be employed for the production of solutions or suspensions of cyanuric chloride since their residence time in the tubular container as well as the temperatures of production can be held very low.

Unless otherwise indicated all parts and percentages are by weight.

The process can comprise, consist essentially of or consist of the steps set forth and the materials can comprise, consist essentially of or consist of those set forth.

The invention will be further explained through the following examples.

DESCRIPTION OF THE PREFERRED EMBODIMENTS

EXAMPLE 1

Liquid cyanuric chloride at about 165° C. was led via the heated supply line 1 into the unary nozzle 3. This nozzle 3 had a bore of 2.4 mm and a spray angle of about 90°. The supply pressure of the liquid cyanuric chloride was 6.5 bar. There were sprayed 320 kg/h of liquid cyanuric chloride through the nozzle 3 into the mixing chamber 5. This mixing chamber 5 had a diameter of 100 mm, the pressure of the mixing chamber was 0.13 bar.

1070 liters/h of toluene via four different supply lines 7 arrived at the chamber segments 9 and after leaving from eight small tubes 8 formed a liquid layer 4 in the mixing chamber 5.

The suspension of cyanuric chloride and toluene left the mixing chamber 5 through the pipe 12. The concentration of cyanuric chloride was 25.7%.

The particle spectrum determined photographically showed 90% of the particles as less than 10 microns.

EXAMPLE 2

Liquid cyanuric chloride at about 170° C. was led via the heated supply line 1 into the unary nozzle 3. This nozzle 3 had a bore of 2.6 mm and a spray angle of about 78°. The supply pressure of the liquid cyanuric chloride was 4.5 bar. There was sprayed 340 kg/h of liquid cyanuric chloride through the nozzle 3 into the mixing chamber 5. This mixing chamber 5 had a diameter of 100 mm, the pressure of the mixing chamber was 0.13 bar.

1100 liters/h of acetone via four different supply lines 7 arrived at the chamber segments 9 and after leaving from eight small tubes formed a liquid layer 4 in the mixing chamber 5.

The suspension of cyanuric chloride and acetone left the mixing chamber 5 through pile 12. The concentration of cyanuric chloride in the suspension was 28.4 weight %; the temperature of the discharging suspension was 14° C.

The particle spectrum determined photographically did not show any particles above 100 microns.

EXAMPLE 3

Liquid cyanuric chloride at about 170° C. was led via the heated supply line 1 into the unary nozzle 3. The nozzle had a bore 3 of 0.8 mm and a spray angle of about 78°. The supply pressure of the melt was 6 bar. There were sprayed 49 kg/h of cyanuric chloride through the nozzle into the mixing chamber 5. The mixing chamber 5 had a diameter of 80 mm and the pressure prevailing in it was 4 bar.

610 liters/h of liquid n-butane via four different supply lines 7 reached the mixing chamber 5 via eight small tubes 8.

The discharging mixture went to an intermediate container. From this intermediate container it was conveyed into a pressure releasing container where the n-butane was evaporated at a pressure of 0.1 bar. The powdery cyanuric chloride remaining had a particle size of more than 95% below 100 microns.

The entire disclosure of German priority application No. P 28 50 243.4-44 is hereby incorporated by reference.

What is claimed is:

1. A process for the production of a suspension or solution of cyanuric chloride in a pure organic solvent containing less than 0.1 weight % of water, comprising spraying cyanuric chloride downwardly and outwardly at a temperature in its molten range from the upper portion of a vertical tubular zone closed at the top thereof to contact and mix with said organic solvent which forms a liquid layer defining said tubular zone, constricting said layer in breast-shaped manner downwardly below the place of entry of the cyanuric chloride into the tubular zone to form a narrower discharge opening; discharging said organic solvent as a spray tangentially to said layer and directed slightly upwardly in the direction of the closed top above said constriction and below the point of introduction of the cyanuric chloride and thereby forming said liquid layer along the entire tubular zone to the point of introduction of the cyanuric chloride, whereby the thickness of said layer where it is formed in breast-shaped constriction is greater than it is in the remainder of the tubular zone.

2. The process of claim 1 wherein the liquid cyanuric chloride employed is free from chlorine or cyanogen chloride.

3. The process of claim 1 wherein the solvent is an ether, hydrocarbon or halohydrocarbon.

4. The process of claim 3 wherein the solvent is dioxane, benzene, toluene or methylene chloride.

5. The process of claim 4 wherein the solvent is toluene.

6. The process of claim 1 including reducing the pressure to between below atmospheric pressure and 0.01 bar and thereby lowering the mixing temperatures.

7. A process according to claim 1 comprising discharging the solution or suspension formed to another container adapted for use at subatmospheric or superatmospheric pressure.

* * * * *